United States Patent
Okugawa

(12) 
(10) Patent No.: US 6,433,353 B2
(45) Date of Patent: Aug. 13, 2002

(54) METHOD AND APPARATUS FOR INSPECTING SURFACE IRREGULARITIES OF TRANSPARENT PLATE

(75) Inventor: Shinya Okugawa, Mie (JP)

(73) Assignee: Central Glass Company, Limited, Ube (JP)

(*) Notice: Subject to any disclaimer, the term of this patent is extended or adjusted under 35 U.S.C. 154(b) by 0 days.

(21) Appl. No.: 09/947,545

(22) Filed: Sep. 7, 2001

Related U.S. Application Data

(62) Division of application No. 09/384,293, filed on Aug. 26, 1999.

(30) Foreign Application Priority Data

Aug. 31, 1998 (JP) ............................................. 10-246231
Jul. 6, 1999 (JP) ............................................. 11-191167

(51) Int. Cl.⁷ .............................................. G01N 21/88
(52) U.S. Cl. ............................. 250/559.4; 250/559.46; 356/239.7
(58) Field of Search ............................. 250/225, 223 R, 250/221, 559.08, 559.09, 559.4, 559.41, 559.42, 559.43, 559.46; 356/364, 369, 600, 601, 445, 239.7, 239.8

(56) References Cited

U.S. PATENT DOCUMENTS

| | | | |
|---|---|---|---|
| 5,016,099 A | 5/1991 | Bongardt et al. | 358/106 |
| 5,245,403 A * | 9/1993 | Kato et al. | 250/559.09 |
| 5,413,941 A * | 5/1995 | Koos et al. | 438/16 |
| 5,521,692 A | 5/1996 | Bares | 355/311 |

FOREIGN PATENT DOCUMENTS

| | | | |
|---|---|---|---|
| EP | 0 575 095 | 12/1993 | |
| JP | 1-122338 | * 8/1989 | ......... G01N/21/88 |
| JP | 1-212338 | 8/1989 | |
| JP | 5-272949 | 10/1993 | |
| JP | 6-167322 | 6/1994 | |
| JP | 7-128032 | 5/1995 | |

* cited by examiner

*Primary Examiner*—Kevin Pyo
(74) *Attorney, Agent, or Firm*—Crowell & Moring LLP

(57) ABSTRACT

A beam of light from a light source is irradiated toward a surface of a transparent plate at an angle of incidence ranging from 86 to 89 degrees or at an angle of incidence ranging from 60 to 89 degrees after being polarized as a P-polarized light beam or S-polarized light beam by a polarizing element disposed between the light source and the transparent plate. This enables a reflected image from a front surface of the transparent plate to be projected on a screen without being influenced by reflection from a rear surface of the transparent plate. By visually inspecting the reflected image on the screen, or by picking up the reflected image by a camera and visually inspecting a picture on a monitor display, or by picking up the reflected image by a camera to obtain density signals representative of the reflected image and calculating the irregularities of the surface of the transparent plate on the basis of the density signals by an image processor.

7 Claims, 6 Drawing Sheets

METHOD AND APPARATUS FOR INSPECTING SURFACE IRREGULARITIES OF TRANSPARENT PLATE

This application is a division of co-pending application Ser. No. 09/384,293, filed Aug. 26, 1999.

BACKGROUND OF THE INVENTION

1. Field of the Invention

The present invention relates to a method of and apparatus for inspecting the surface irregularities of a transparent plate such as a plate of glass and a plate of resin, particularly a glass plate for use in a liquid crystal display.

2. Description of the Related Art

A glass sheet or plate made by the known float process has an excellent surface smoothness and flatness so it is used widely other than being used as window glass for automotive vehicles and buildings. Particularly, a glass plate for use in a liquid crystal display is required to be small in the surface irregularities, so it is necessitated to be ground further after being made or formed by the float process.

For inspection of the surface irregularities of such a glass plate, it is frequently used a method of irradiating a beam of light onto a surface of a glass plate and projecting a reflected beam of light from the surface of the glass plate on a screen for inspection, as disclosed in Japanese Patent Provisional Publication Nos. 1-212338, 5-272949 and 7-128032.

Japanese Patent Provisional Publication No. 1-212338 discloses an apparatus for measuring the surface irregularities of an ordinary glass plate wherein a beam of light is irradiated onto the glass plate at an angle of incidence ranging from 70 to 85 degrees. In this instance, the term "angle of incidence" indicates the angle formed by a beam of light arriving at a surface and the perpendicular to that surface at the point of arrival.

Japanese Patent Provisional Publication No. 5-272949 discloses a method of evaluating the properties of a glass plate required to have a high flatness or eveness for use in a liquid crystal display. In this method, an optical multi-line surface irregularity measuring apparatus including an optical displacement meter made up of a laser beam source and a line sensor is used for measuring the surface irregularities of the ground surfaces of the glass plate.

The Japanese Patent Provisional Publication No. 7-128032 discloses a method of inspecting the waviness of the surfaces of a glass plate for a liquid crystal display wherein an ultraviolet ray is irradiated onto a glass plate in order to eliminate reflection from the rear surface of the glass plate.

In this instance, the rear surface reflection means, as shown in FIG. 7, that the beam of light incident onto the plane of incidence (front surface) is transmitted through the transparent body and reflected by the rear surface to go back to the plane of incidence again. Thus, if there is a beam of light reflected by the rear surface, the reflected light from the transparent body contains not only the information on the surface irregularities of the front surface but the information on the surface irregularities of the rear surface, thus causing a problem that accurate information on the surface irregularities of the front surface cannot be attained.

For example, a problem of the measurement device disclosed by Japanese Patent provisional Publication No. 1-212338 is that since the beam of light is irradiated onto the glass sheet at an angle of incidence ranging from 70 to 85 degrees it is incapable of avoiding the influence of the reflected beam of light from the rear surface and therefore accurate measurement of the surface irregularities cannot be attained.

The method disclosed by Japanese Patent Provisional Publication No. 5-272949 considers nothing about the reflection by the rear surface of the glass plate, thus causing a problem that an erroneous measurement due to reflection of a laser beam from the rear surface of the glass plate is unavoidable and furthermore use of a laser beam inevitably leads to an expensive cost of the device.

Further, the method disclosed by Japanese Patent Provisional Publication No. 7-128032, though it can eliminate reflection of light from the rear surface of the glass plate, requires a light source of particular short-wavelength ultraviolet rays and furthermore a screen to which a fluorescent material is applied, thus causing a problem that a costly device is necessitated and further an operator is needed to take care in handing the device so that his eyes and skin are not damaged by ultraviolet rays irradiated.

SUMMARY OF THE INVENTION

It is accordingly an object of the present invention to provide a method of detecting front surface irregularities of a glass plate which enables to attain accurate detection by preventing rear surface reflection by the use of a light source and screen which are not of the particular kinds but usually used.

It is a further object of the present invention to provide an apparatus for carrying out the method of the foregoing character.

To achieve the above object, the present invention provides a method of inspecting surface irregularities of a transparent plate comprising irradiating a beam of light from a light source toward a surface of the transparent plate at an angle of incidence ranging from 86 to 89 degrees, projecting a reflected image of the beam from the surface of the transparent plate on a screen, and inspecting irregularities of the surface of the transparent plate on the basis of the reflected image projected on the screen.

According to another aspect of the present invention, there is provided a method of inspecting surface irregularities of a transparent plate comprising irradiating a beam of light from a light source toward a surface of the transparent plate at an angle of incidence ranging from 60 to 89 degrees, polarizing the beam of light from the light source by a polarizing element disposed between the light source and the transparent plate so that the beam of light from the light source is incident on the surface of the transparent plate as one of a P-polarized light beam and an S-polarized light beam, projecting a reflected image of the beam from the surface of the transparent plate on a screen, and inspecting irregularities of the surface of the transparent plate on the basis of the reflected image projected on the screen.

In the above described method of inspecting surface irregularities of a transparent plate, the angle of incidence of the S-polarized light beam and the angle of incidence of the P-polarized light beam are in the range from:

85 to 89 degrees and 87 to 89 degrees when a visible ray transmittance of the glass plate is 90% or more and less than 100%, respectively;

84 to 89 degrees and 87 to 89 degrees when the visible ray transmittance is 80% or more and less than 90%, respectively;

83 to 89 degrees and 87 to 89 degrees when the visible ray transmittance is 70% or more and less than 80%, respectively;

81 to 89 degrees and 86 to 89 degrees when the visible ray transmittance is 60% or more and less than 70%, respectively;

78 to 89 degrees and 84 to 89 degrees when the visible ray transmittance is 50% or more and less than 60%, respectively;

72 to 89 degrees and 82 to 89 degrees when the visible ray transmittance is 40% or more and less than 50%, respectively;

60 to 89 degrees and 75 to 89 degrees when the visible ray transmittance is 30% or more and less than 40%, respectively; and 60 to 89 degrees and 60 to 89 degrees when the visible ray transmittance is less than 30%, respectively.

According to a further aspect of the present invention, there is provided an apparatus for inspecting surface irregularities of a transparent plate comprising a light source irradiating a beam of light toward a surface of the transparent plate at an angle of incidence ranging from 86 to 89 degrees, and a screen on which a reflected image of the beam of light from the surface of the transparent plate is projected.

According to a still further aspect of the present invention, there is provided an apparatus for inspecting surface irregularities of a transparent plate comprising a light source irradiating a beam of light toward a surface of the transparent plate at an angle of incidence ranging from 60 to 89 degrees, a polarizing element capable of adjusting a polarizing angle, disposed between the light source and the transparent plate so that the beam of light from the light source is incident on the surface of the transparent plate as a polarized light beam, a screen on which a reflected image of the polarized light beam from the surface of the transparent plate is projected, and inspecting means for inspecting the surface irregularities of the transparent plate on the basis of the reflected image projected on the screen.

DETAILED DESCRIPTION OF THE PREFERRED EMBODIMENT

Figure 1:
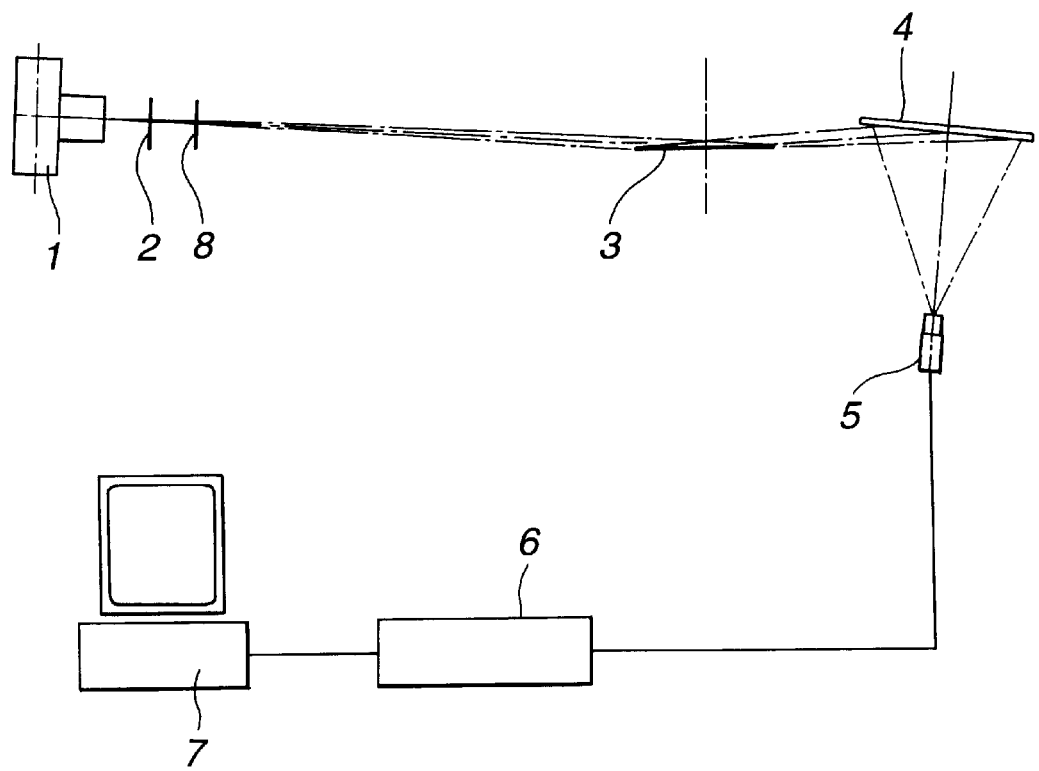
FIG. 1 is a schematic elevational view of an apparatus for detecting irregularities of a surface of a transparent plate according to an embodiment of the present invention.
Figure 2:
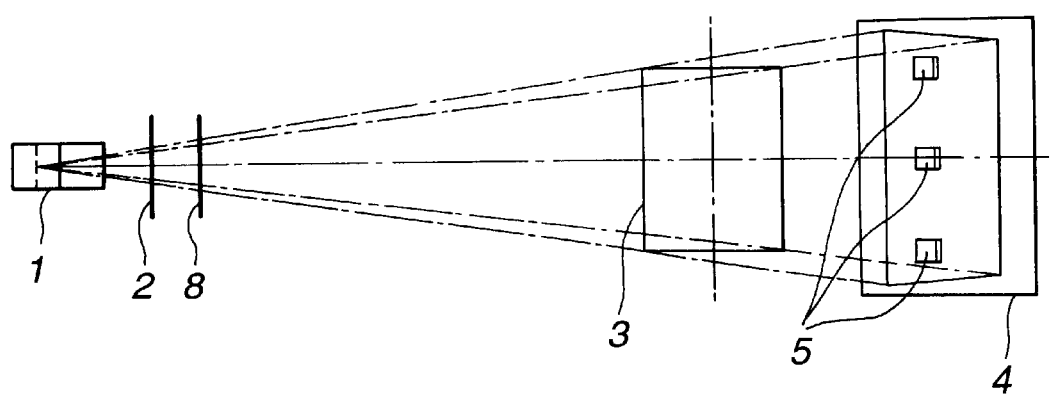
FIG. 2 is a schematic plan view of the apparatus of FIG. 1.

Referring first to FIGS. 1 and 2, an apparatus for inspecting surface irregularities of a transparent plate according to an embodiment of the present invention will be described. The apparatus is adapted for adoption to such a case where a beam of light from a light source is passed through a polarizing plate so as to be polarized as an S-polarized light beam.

The apparatus includes a light source 1 such as a high pressure mercury vapor lamp, a polarizing plate 2 disposed in front of the light source 1 for obtaining an S-polarized light beam, a screen 4 on which a reflected image of the beam from a transparent plate 3 such as a glass substrate is projected, a set of cameras 5 such as CCD cameras for picking up the reflected image projected on the screen 4, an image processor 6 for receiving signals from the cameras 5 and inspecting the surface irregularities of the transparent plate 3 on the basis of the signals, and a personal computer 7.

Actually, a diaphragm 8 is disposed in front of the polarizing plate 2 so as to prevent the beam of light from the light source 1 from being directly irradiated upon the screen 4.

In this instance, the transparent plate 3 is supported on a support (not shown) which is disposed nearly horizontally and positioned so that the angle of incidence of the S-polarized light toward the transparent plate 3 is within the range from 60 to 89 degrees. Preferably, the range of angle of incidence is set depending upon the visible ray transmittance of the transparent plate 3.

Figure 3:
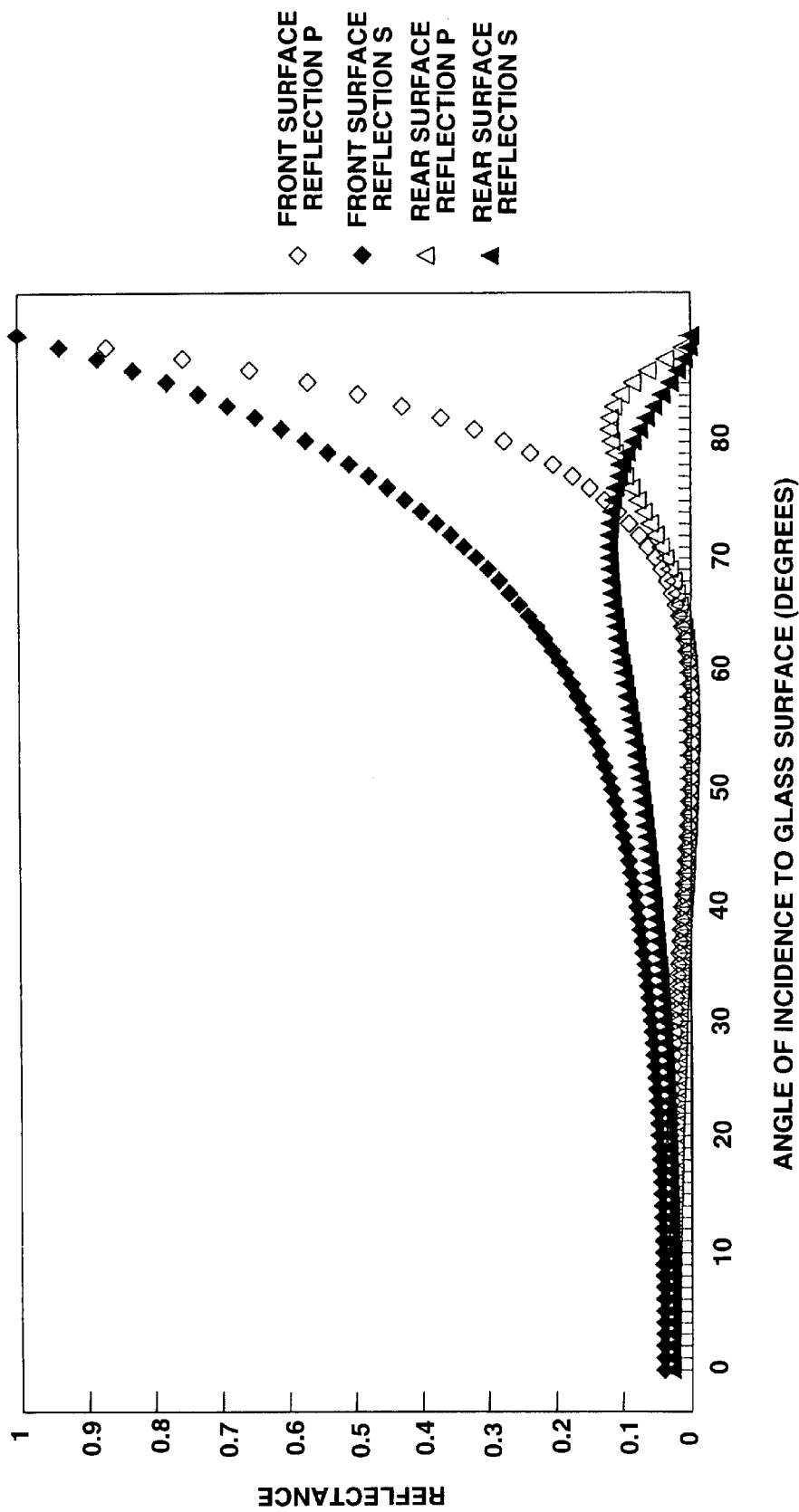
FIG. 3 is a graph of reflection characteristics of a front surface and a rear surface of a transparent plate in case a visible ray transmittance of the transparent plate is 90% and an S-polarized light and P-polarized light are used as a light source.
Figure 5:
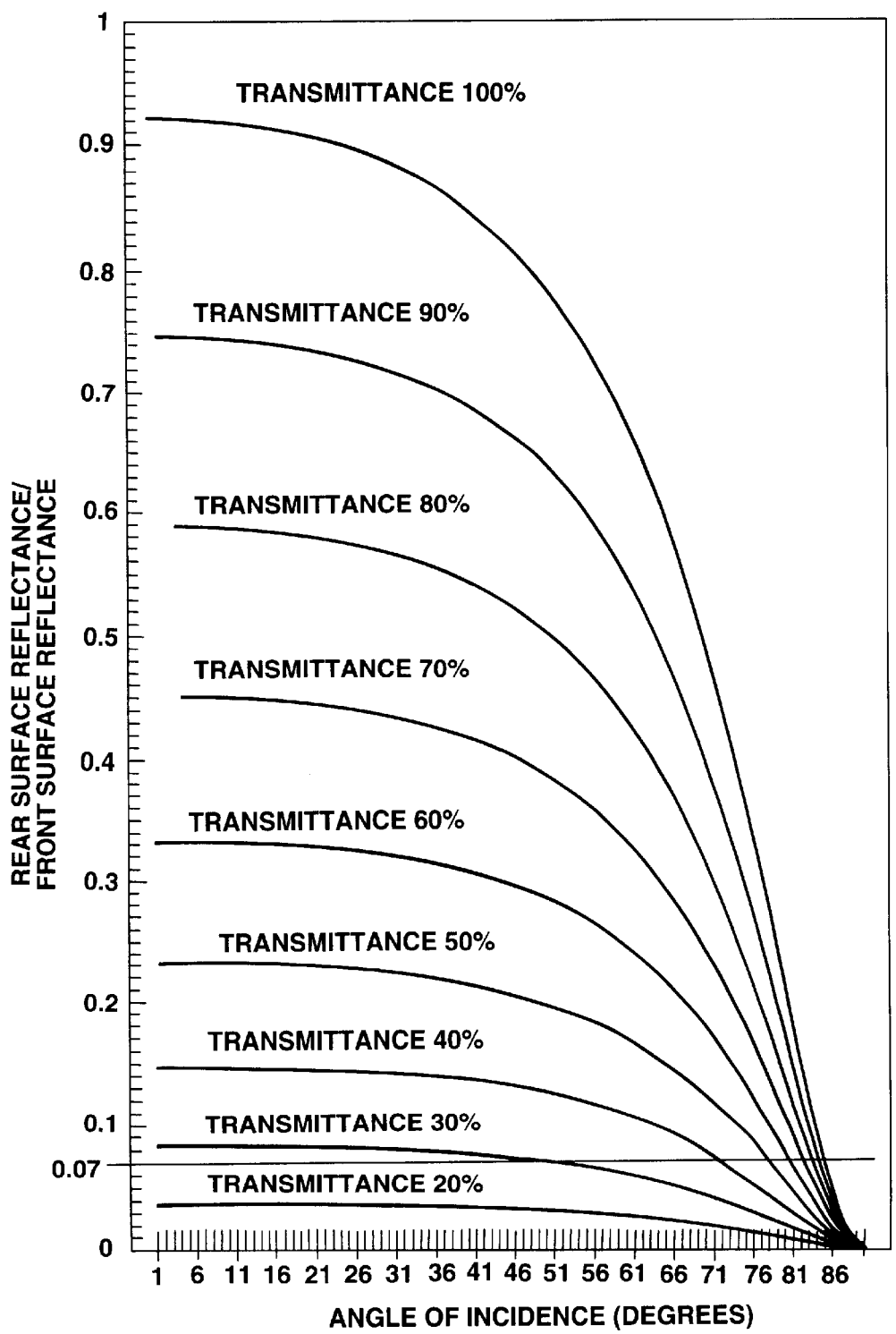
FIG. 5 is a graph of a ratio of a rear surface reflectance to a front surface reflectance in case a S-polarized light is incident on each front surface of various transparent plates having different visible ray transmittances.
Figure 6:
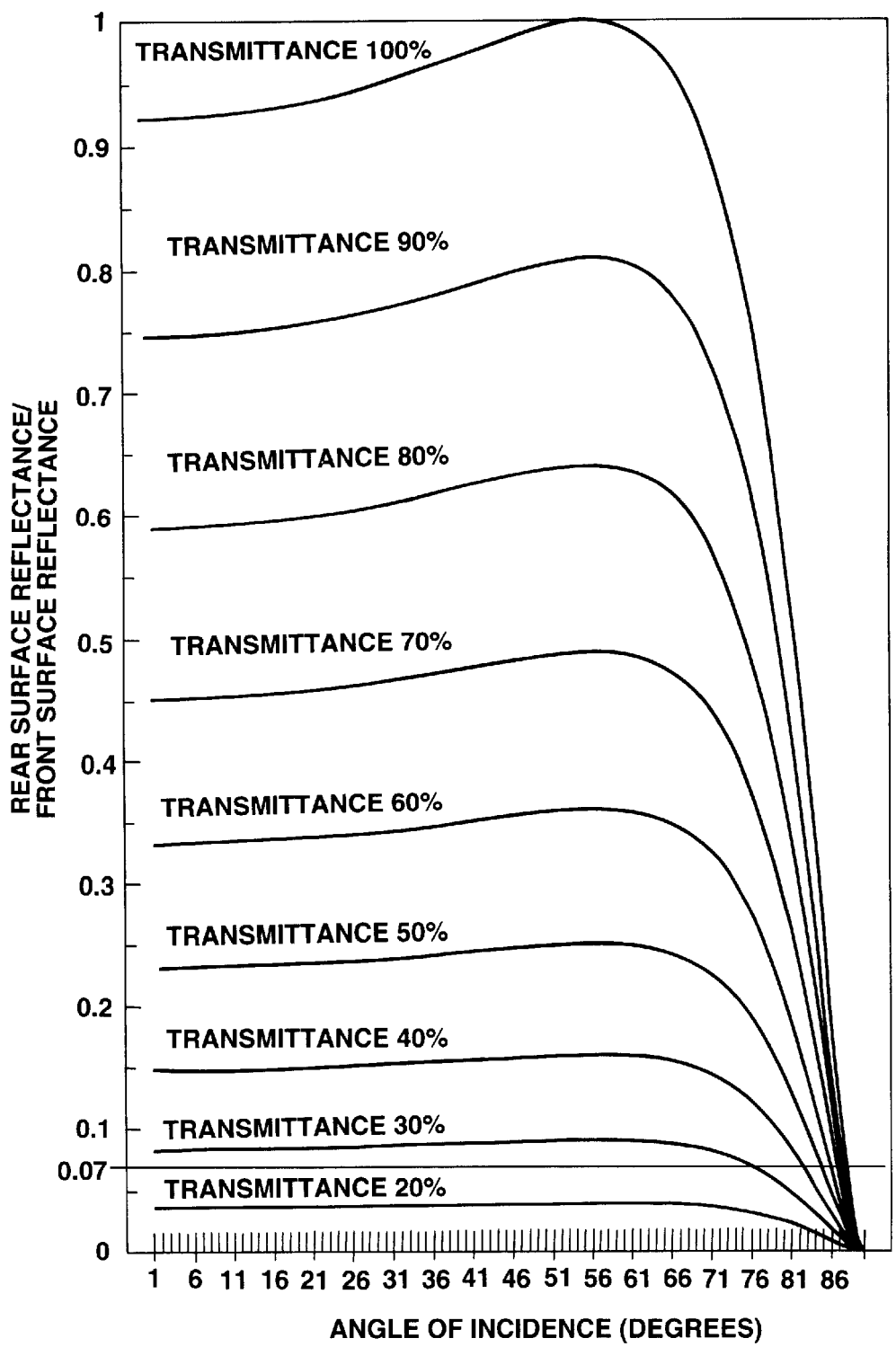
FIG. 6 is a graph of a ratio of a rear surface reflectance to a front surface reflectance in case a P-polarized light is incident on each front surface of various transparent plates having different visible ray transmittances.
Figure 7:
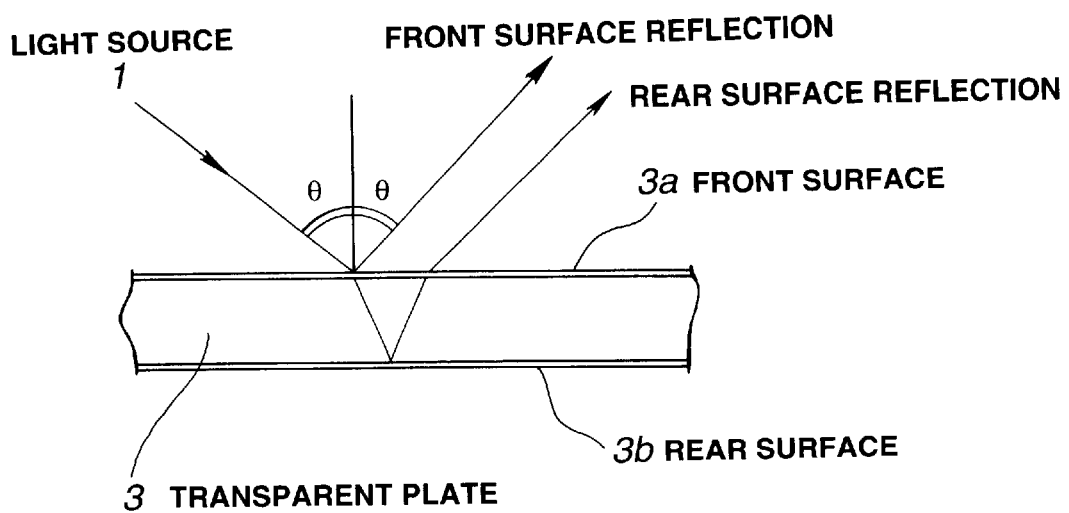
FIG. 7 is an illustration of reflection of light from a front surface and a rear surface of a transparent plate when a light abeam is incident upon the transparent plate.

FIG. 3 shows reflection characteristics of a front surface and a rear surface of a transparent plate in case an incident light is an S-polarized light or P-polarized light, as an example of a case where reflection from the rear surface is large, in which the transparent plate is a float glass plate or the like which is 3 mm thick and has a visible ray transmittance of 90%. Referring to FIGS. 5 and 6, it will seen that the angle of incidence which allows the ratio of the reflectance of the rear surface to that of the front surface is 7% or less ranges from 85 to 89 degrees in case of the S-polarized incident light and 87 to 89 degrees in case of the P-polarized incident light.

Figure 4:
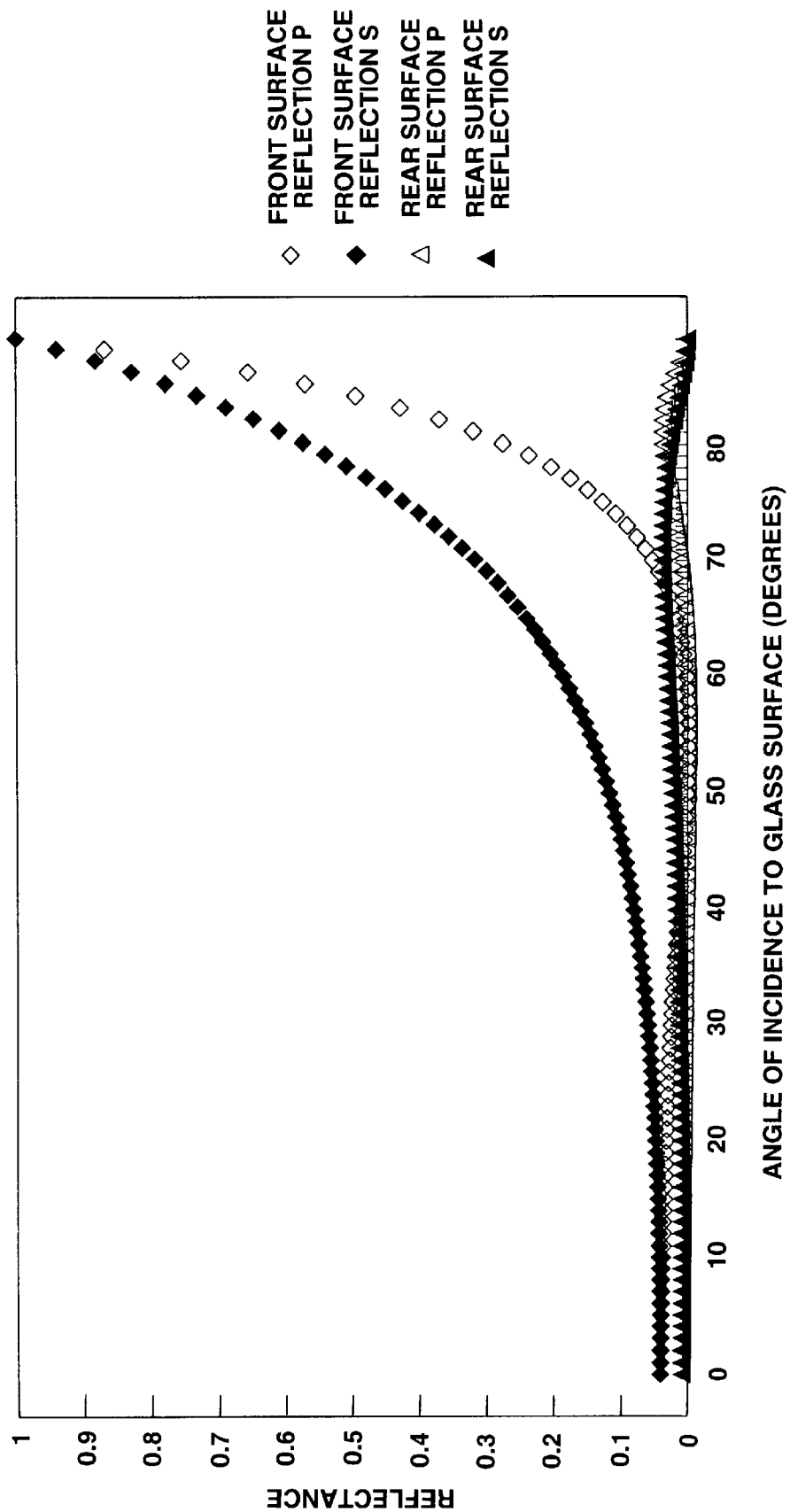
FIG. 4 is a graph of reflection characteristics of a front surface and a rear surface of a transparent plate in case a visible ray transmittance of the transparent plate is 50% and a S-polarized light and P-polarized light are used as a light source.

FIG. 4 shows reflection characteristics of a front surface and a rear surface of a transparent plate in case of an S-polarized incident light and P-polarized incident light, as an example of a case where reflection from the rear surface is small, in which the transparent plate has a visible ray transmittance of 50%. From FIGS. 5 and 6, it will seen that the angle of incidence which allows the ratio of the reflectance of the rear surface to that of the front surface is 7% or less ranges from 78 to 89 degrees in case of the S-polarized incident light and 84 to 89 degrees in case of the P-polarized incident light.

In such an apparatus, when a beam of light is irradiated from the light source 1, the reflected image of the beam from the transparent plate 3 is projected on the screen 4, wherein reflection from the rear surface is almost negligible.

When the reflected image on the screen 4 is picked up by the cameras 5 such as CCD cameras, a picked up image has a central portion which is bright and a portion which becomes darker as it goes nearer to the periphery thereof due to uneveness of illumination since the light source in this embodiment is nearly a point source of light. Thus, by previously storing such a light and dark pattern of the image in the image processor 6 and allowing the image processor 6 to calculate the difference between density signals taken for inspection and reference density signals resulting from the stored light and dark pattern, an influence of uneven illumination of the light source can be removed.

The density signals obtained in this manner generally causes a plurality of vertical or horizontal, light and dark stripes corresponding to the surface irregularities of the transparent plate 3.

Thus, by the image processor, all of the pixels are scanned in the horizontal or vertical direction perpendicular to the direction in which the stripes are elongated, whereby to obtain, from the density signals of the pixels on each scanning line, a waveform representative of the density. By calculating the difference between the peak and valley of the waveform wavelength, etc., the surface irregularities of the entire transparent plate are inspected and displayed as data of the personal computer 7, recorded or printed according to the necessity.

In this instance, in the image processor 6, the waveform representative of the density is subjected to the process using a band pass filter and the process of moving averages, whereby to remove an influence of waviness, warping, etc.

The waveform representative of the density corresponding to the surface irregularities of the transparent plate, which is to be inspected in the above manner, is quite similar to a measured profile obtained by a contact type surface roughness tester, so that it was confirmed that quite accurate measurement could be obtained.

From the foregoing, it will be understood that the present invention is a method of and apparatus for detecting surface irregularities of a transparent plate by irradiating a beam of light from a light source toward a front surface of the transparent plate at a predetermined angle of incidence so that no substantial reflection is caused by a rear surface, projecting only a reflected image of the beam from the front surface on a screen and determining irregularities of the front surface of the transparent plate on the basis of the reflected image projected on the screen. Between the light source and the transparent plate is disposed a polarizing plate according to the necessity so that the beam of light from the light source is used as an ordinary light which is not polarized by the polarizing plate or the beam of light from the light source is polarized as a S-polarized light beam or the beam of light from the light source is polarized as a P-polarized light beam. Depending upon a visible ray transmittance of a transparent plate, the kind of light irradiated upon the transparent plate is selected suitably for thereby adjusting the angle of incident at which the light from the light source is irradiated to the transparent plate.

The requirement that no substantial reflection from a rear surface of a transparent plate but only reflection from a front surface occurs can be met if there is not caused scarcely any influence of reflection from the rear surface. That is, in case the ratio of the rear surface reflectance to the front surface reflectance is less than 7%, there is not caused scarcely any influence of reflection by the rear surface, so such a condition is hereinafter referred to as a state in which there is not any rear surface reflection.

The screen is arranged in parallel to a front surface of the transparent plate to be inspected and at such a position that when a beam of light from a light source is incident upon the front surface of the transparent plate to reflect therefrom a reflected image of the entire front surface can be projected upon the screen.

The transparent plate and screen can be arranged vertically other than being arranged horizontally as described above.

A method of inspecting surface irregularities of a transparent plate can include either of a step of visually inspecting the reflected image projected on the screen, a step of picking up the reflected image projected on the screen by a CCD camera or the like and visually inspecting the picture on a monitor display or a step of picking up the reflected image by a CCD camera to obtain density signals representative of the irregularities of the surface of the transparent plate and calculating the irregularities of the surface of the transparent plate by an image processor. However, visual inspection causes variations depending upon the skill of an inspector, so use of an image processor is desirable since more accurate measurement is obtained.

In case an ordinary light is used without using a polarizing plate, the light is transmitted toward the transparent plate at an angle of incidence ranging from 86 to 89 degrees. By this, in a state where the influence of reflection from the rear surface of the transparent plate is eliminated, the reflected image from the front surface of the transparent plate is projected on the screen. The reflected image of the front surface of the transparent plate projected on the screen is inspected visually or by using a CCD camera or by using an image processor to detect the surface irregularities of the transparent plate as described above.

In case an ordinary light which is not processed by a polarizing plate is irradiated to a transparent substrate, an influence of rear surface reflection results when the angle of incident is smaller than 86 degrees and it becomes difficult to measure the surface irregularities when the angle of incidence is larger than 89 degrees since the incident light is almost parallel to the front surface of the transparent substrate, so the angle of incidence is set so as to range from 86 to 89 degrees. So long as the angle of incidence is within this range, it becomes possible to reduce the reflection from the rear surface of the transparent substrate to such an extent as to be negligible and measure the surface irregularities accurately even by using an ordinary light.

However, the smaller the angle of incidence the clearer the reflected image, so the smaller angle range, i.e., the range from 86 to 87 degrees is desirable.

In case a polarized light which is polarized by using a polarizing plate is used, a beam of light from the light source is polarized by a polarizing element such as a polarizing plate disposed between the light source and a transparent plate, as an S-polarized light beam or a P-polarized light beam. In this instance, the beam of light from the light source is irradiated toward the transparent plate at an angle of incidence ranging from 60 to 89 degrees. The beam of light from the light source is incident on the surface of the transparent plate as an S-polarized light beam or P-polarized light beam. The reflected image of the beam from the transparent plate is projected on the screen such that the surface irregularities of the transparent plate are detected on the basis of the reflected image which is projected on the screen to represent the surface irregularities of the transparent plate.

In this instance, it is desirable to set the angle of incidence depending upon whether an incident light beam is an S-polarized light beam or a P-polarized light beam and upon stepwise ranges of visible ray transmittances of transparent plates (hereinafter referred to simply as transmittance). That is, it is desirable that the angle of incidence of the S-polarized light beam and the angle of incidence of the P-polarized light beam are in the range from:

85 to 89 degrees and 87 to 89 degrees when a visible ray transmittance of the glass plate is 90% or more and less than 100%, respectively;

84 to 89 degrees and 87 to 89 degrees when the visible ray transmittance is 80% or more and less than 90%, respectively;

83 to 89 degrees and 87 to 89 degrees when the visible ray transmittance is 70% or more and less than 80%, respectively;

81 to 89 degrees and 86 to 89 degrees when the visible ray transmittance is 60% or more and less than 70%, respectively;

78 to 89 degrees and 84 to 89 degrees when the visible ray transmittance is 50% or more and less than 60%, respectively;

72 to 89 degrees and 82 to 89 degrees when the visible ray transmittance is 40% or more and less than 50%, respectively;

60 to 89 degrees and 75 to 89 degrees when the visible ray transmittance is 30% or more and less than 40%, respectively; and 60 to 89 degrees and 60 to 89 degrees when the visible ray transmittance is less than 30%, respectively.

This is because in case of a colored transparent plate such as a colored glass plate the visible ray transmittance becomes lower due to coloring so that the influence of rear surface reflection can be smaller even when the angle of incidence becomes smaller and therefore the range of the angle of incidence can be wider.

Further, even if the material of the same transmittance is used, the transmittance of the transparent plate becomes lower as the thickness becomes thicker. Thus, the range of angle of incidence can be wider as the transparent plate becomes thicker.

In this manner, when the light polarized by the polarizing plate is irradiated, a considerable influence of reflection of the rear surface is caused, as seen from FIGS. 3 to 6 which show reflection characteristics representative of reflectance of the front surface and the reflectance of the rear surface of the transparent plate, when the angle of incidence is less than 60 degrees. However, when the angle of incidence is more than 89 degrees, the light is incident upon the transparent plate nearly in parallel thereto so that it is difficult to carry out detection of the surface irregularities, so that the angle of incidence is set so as to range from 60 to 89 degrees. When the angle of incidence is set within this range, the reflectance of the front surface of the transparent plate increases abruptly, whereas the reflectance of the rear surface reduces to a considerably small value, so inspection of the surface irregularities can be done without scarcely any influence of reflection of the rear surface.

However, the range of angle of incidence which enables inspection of the surface irregularities varies depending upon the visible ray transmittance of the transparent plate so it will suffice to set the angle of incidence of the light from the light source, having transmitted through the polarizing plate, to an optimal value depending upon the range of transmittance.

As the source of light, a high pressure mercury vapor lamp, a xenon lamp or the like closely allied to a point source of light, and a light source unit including optical instruments such as one of various light sources, a cylindrical lens, a convex lens and a concave mirror which are combined so as to produce parallel light beams, can be suitably employed.

Regarding whether the light from the light source is to be polarized or not, it is advantageous to use an S-polarized light since the reflected image becomes clearer as the incident angle becomes smaller. However, a P-polarized light or an ordinary light which is not polarized can of course be used.

In case the light from the light source is to be polarized, it will suffice to place a polarizing element such as a polarizing plate in front of the light source for polarization.

The transparent plate which is an object for inspection can be a plate of transparent resin such as acrylic resin and polycarbonate, other than a glass plate.

As the screen, anything other than one made of a lusterless white paper, metal or cloth can be used so long as a reflected image can be projected on it. In this connection, a lusterless screen is preferable.

In case a camera is used, a two-dimensional camera such as an ordinary CCD camera can be employed suitably. However, a one-dimensional camera such as a line sensor which is adapted to move along horizontal lines can be used.

In this instance, a plurality of cameras, the number of which is determined based on the size of the transparent plate, are disposed to pick up the density signals on the screen.

A single CCD camera will suffice if the transparent plate is of the usual size, i.e., about 250 mm square.

While the transparent plate is disposed horizontally in the embodiment which will be described hereinlater, it can be disposed vertically or obliquely. However, it is more desirable to dispose the transparent plate at the same inclined or not inclined position as a liquid crystal display or the like in which it is actually used.

While it is desirable to dispose the camera at such a position where it can pick up the reflected image from the front surface of the screen on which the reflected image is projected, it will suffice to employ an opaque screen and allow the reflected image to be picked up from the rear surface of the screen.

The image processing after the reflected image on the screen is picked up by the camera can be done in a well known manner. For example, if a light source closely allied to a point source of light is used, uneven irradiation of the light source causes the reflected image to have a central portion which is bright and a peripheral portion which becomes darker as it goes nearer to a peripheral edge thereof. The density signals representative of such an uneven brightness is stored in an image processing unit as reference signals. In the image processing unit, the difference between the density signals picked up by the camera (e.g., 255 gradations of density signals per 512 pixels×512 pixels) and the reference density signals are calculated per respective pixels for thereby eliminating the influence of the uneven radiation of the light source.

As a result, the density signals appear cyclically in the vertical direction (or in the horizontal direction) in accordance with the surface irregularities of the transparent plate. While the reflected image projected on the screen is actually trapezoid in case a point source of light is used (though the reflected image is rectangular in case the light source radiates parallel light beams), it is formed into a rectangular shape through transformation of the coordinates of the image since the transparent plate and the reflected image have a fixed positional relationship so that each portion of the transparent plate can correspond to each portion of the reflected image. Thereafter, the density signals in every horizontal scanning line (or vertical scanning line) are read to obtain waveforms representative of the densities for the respective horizontal scanning lines (or for the respective vertical scanning lines). From the difference between the peak and valley of the waveform, a value representative of the surface roughness (Rmax) or waviness corresponding to the magnitude of the surface irregularities can be measured.

In this instance, the waveform representative of the waviness of the transparent plate may exist as a noise and be superimposed on the waveform representative of the surface irregularities. Thus, it is desirable to remove the influence of noise due to existence of the waveform other than that for measurement by the process using a band pass filter or the process of moving averages.

The image processor will suffice if it has a storing function, computing function and inputting and outputting function. If the image processor has a displaying function, the personal computer shown in the embodiment can be dispensed with.

Further, the personal computer may additionally be provided with a board for input of image so as to be used as an image processor.

Regarding the term "S-polarized light" and the term "P-polarized light", a polarized light having a plane of vibration perpendicular to the plane of incidence (the plane of incidence is not a surface of a transparent plate or the like but indicates a plane containing electric vector of light wave) is referred to as an S-polarized light and one having a plane of vibration parallel to the plane of incidence is referred to as a P-polarized light. P and S are the first letters of German words of "Senkrecht" and "Parallel", respectively.

From the foregoing, it will be understood that the method of and apparatus for inspecting surface irregularities of a transparent plate can do away with the influence of the rear surface reflection completely and attain accurate inspection of the surface irregularities without requiring a particular light source such as one radiating ultraviolet rays but by using an inexpensive apparatus including an ordinary light source and screen.

The present invention has been described in an illustrative manner. It is to be understood that the terminology which has been used is intended to be in the nature of words of description rather than of limitations.

May modifications and variations of the present invention are possible inlight of the above teachings. Therefore, within the scope of the appended claims, the present invention may be practiced otherwise than as specifically described.

What is claimed is:

1. A method of inspecting surface irregularities of a transparent plate comprising:

irradiating a beam of light from a light source toward a surface of the transparent plate at an angle of incidence ranging from 86 to 89 degrees;

projecting a reflected image of said beam from the surface of the transparent plate on a screen; and inspecting irregularities of the surface of the transparent plate on the basis of said reflected image projected on the screen.

2. A method according to claim 1, wherein said inspecting comprises visually inspecting said reflected image.

3. A method according to claim 1, wherein said inspecting comprises picking up said reflected image by a camera and visually inspecting a picture on a monitor display.

4. A method according to claim 1, wherein said inspecting comprises picking up said reflected image by a camera to obtain density signals representative of said reflected image, and calculating the irregularities of the surface of the transparent plate on the basis of said density signals by an image processor.

5. An apparatus for inspecting surface irregularities of a transparent plate comprising:

a light source irradiating a beam of light toward a surface of the transparent plate at an angle of incidence ranging from 86 to 89 degrees; and a screen on which a reflected image of said beam of light from the surface of the transparent plate is projected.

6. An apparatus for inspecting surface irregularities of a transparent plate comprising:

a light source irradiating a beam of light toward a surface of the transparent plate at an angle of incidence ranging from 86 to 89 degrees;

a screen on which a reflected image of said beam of light from the surface of the transparent plate is projected; and means for inspecting the surface irregularities of the transparent plate on the basis of said reflected image projected on said screen.

7. An apparatus according to claim 6, wherein said inspecting means comprises a camera for picking up said reflected image on said screen to obtain density signals representative of said reflected image and an image processor for calculating the irregularities of the surface of the transparent plate on the basis of said density signals.

* * * * *